United States Patent
Li (10) Patent No.: US 12,044,814 B2
(45) Date of Patent: Jul. 23, 2024

(54) CLOSE-RANGE POSITRON EMISSION TOMOGRAPHY MODULES AND SYSTEM

(71) Applicant: Arizona Board of Regents on Behalf of the University of Arizona, Tucson, AZ (US)

(72) Inventor: Xin Li, San Jose, CA (US)

(73) Assignee: Arizona Board of Regents on Behalf of the University of Arizona

( * ) Notice: Subject to any disclaimer, the term of this patent is extended or adjusted under 35 U.S.C. 154(b) by 233 days.

(21) Appl. No.: 17/441,644

(22) PCT Filed: Mar. 20, 2020

(86) PCT No.: PCT/US2020/023940
§ 371 (c)(1),
(2) Date: Sep. 21, 2021

(87) PCT Pub. No.: WO2020/198036
PCT Pub. Date: Oct. 1, 2020

(65) Prior Publication Data
US 2022/0163685 A1     May 26, 2022

Related U.S. Application Data

(60) Provisional application No. 62/822,628, filed on Mar. 22, 2019.

(51) Int. Cl.
*G01T 1/29* (2006.01)
*A61B 6/03* (2006.01)
(Continued)

(52) U.S. Cl.
CPC ............ *G01T 1/2985* (2013.01); *A61B 6/037* (2013.01); *A61B 6/4266* (2013.01);
(Continued)

(58) Field of Classification Search
CPC ..... G01T 1/2985; G01T 1/1644; G01T 1/166; G01T 1/202; A61B 6/037; A61B 6/4266; A61B 6/4275
See application file for complete search history.

(56) References Cited

U.S. PATENT DOCUMENTS 6,362,479 B1 * 3/2002 Andreaco ............. G01T 1/1644
250/363.01
9,029,791 B1   5/2015 Kovalski et al.
(Continued)

FOREIGN PATENT DOCUMENTS

WO    WO 2018/081404    5/2018

OTHER PUBLICATIONS

International Search Report and Written Opinion, Corresponding to International Application No. PCT/US20/23940, Mailed Jun. 17, 2020.
(Continued)

*Primary Examiner* — Kiho Kim
(74) *Attorney, Agent, or Firm* — Leydig, Voit & Mayer, LTD.

(57) ABSTRACT

This invention provides a close-range positron emission tomography (PET) system, where the detector modules are able to be moved or placed very close to the patient compared to conventional PET systems. As a result, the sensitivity and resolution of the PET system is greatly increased.

20 Claims, 9 Drawing Sheets

(51) Int. Cl.
A61B 6/42 (2024.01)
G01T 1/164 (2006.01)
G01T 1/166 (2006.01)
G01T 1/202 (2006.01)

(52) U.S. Cl.
CPC .......... *A61B 6/4275* (2013.01); *G01T 1/1644* (2013.01); *G01T 1/166* (2013.01); *G01T 1/202* (2013.01)

(56) References Cited

U.S. PATENT DOCUMENTS

| | | | |
|---|---|---|---|
| 2004/0031926 A1* | 2/2004 | Ogawa | G01T 1/2985 250/370.06 |
| 2005/0113667 A1 | 5/2005 | Schlyer et al. | |
| 2008/0103391 A1* | 5/2008 | Dos Santos Varela | G01T 1/2985 250/363.04 |
| 2010/0108894 A1* | 5/2010 | Pratx | G01T 1/2985 250/362 |
| 2012/0068076 A1 | 3/2012 | Daghighian | |
| 2014/0276018 A1 | 9/2014 | Mukdadi et al. | |
| 2015/0230766 A1* | 8/2015 | Wang | A61B 5/0035 600/411 |
| 2020/0345322 A1* | 11/2020 | Bai | A61B 6/4266 |

OTHER PUBLICATIONS

Ito et al. (2011) Positron Emission Tomography (PET) Detectors with Depth-of-Interaction (DOI) Capability, Biomed Eng Lett, 1:70-81.

Morrocchi et al. (2017) Depth of interaction determination in monolithic scintillator with double side SiPM readout, EJNMMI Physics, 4:11.

Moses (2011) Fundamental limits of spatial resolution in PET. Nuclear Instruments and Methods in Physics Research Section A: Accelerators, Spectrometers, Detectors and Associated Equipment 648: S236-S240.

Yang et al. (2008) A Prototype PET Scanner with DOI-Encoding Detectors, Journal of Nuclear Medicine, 49 (7) 1132-1140.

* cited by examiner

FIG. 1

Total crystal elements: 27
Total samples per crystal element: 8
Total samples: 27*8=216

Total crystal elements: 16
Total samples per crystal element: 9
Total samples: 16*9=144

Total crystal elements : 20
Total samples per crystal element: 11
Total samples: 20*11 = 220

More blurry due to lack of DOI

Less blurry due to the correction with the help of DOI

Prostate & pelvic scan

FIG. 9

Head scan

CLOSE-RANGE POSITRON EMISSION TOMOGRAPHY MODULES AND SYSTEM

CROSS-REFERENCE TO RELATED APPLICATIONS

This application is a U.S. National Stage Application filed under 35 U.S.C. § 371 of International Application No. PCT/US2020/023940, filed Mar. 20, 2020, which claims priority from U.S. Provisional Patent Application No. 62/822,628, filed Mar. 22, 2019. Both of these applications are hereby incorporated by reference in their entireties.

BACKGROUND OF INVENTION

Positron emission tomography (PET) is a powerful tool primarily used for oncology, cardiology and neurology. PET can provide functional information in addition to structural information about tissues, organs and tumors. However, current PET systems are limited by insufficient gamma-ray collection efficiency (known as sensitivity, which is currently around 0.5%-2.5%) and poor spatial resolution (currently around 4 mm).

Figure 1:
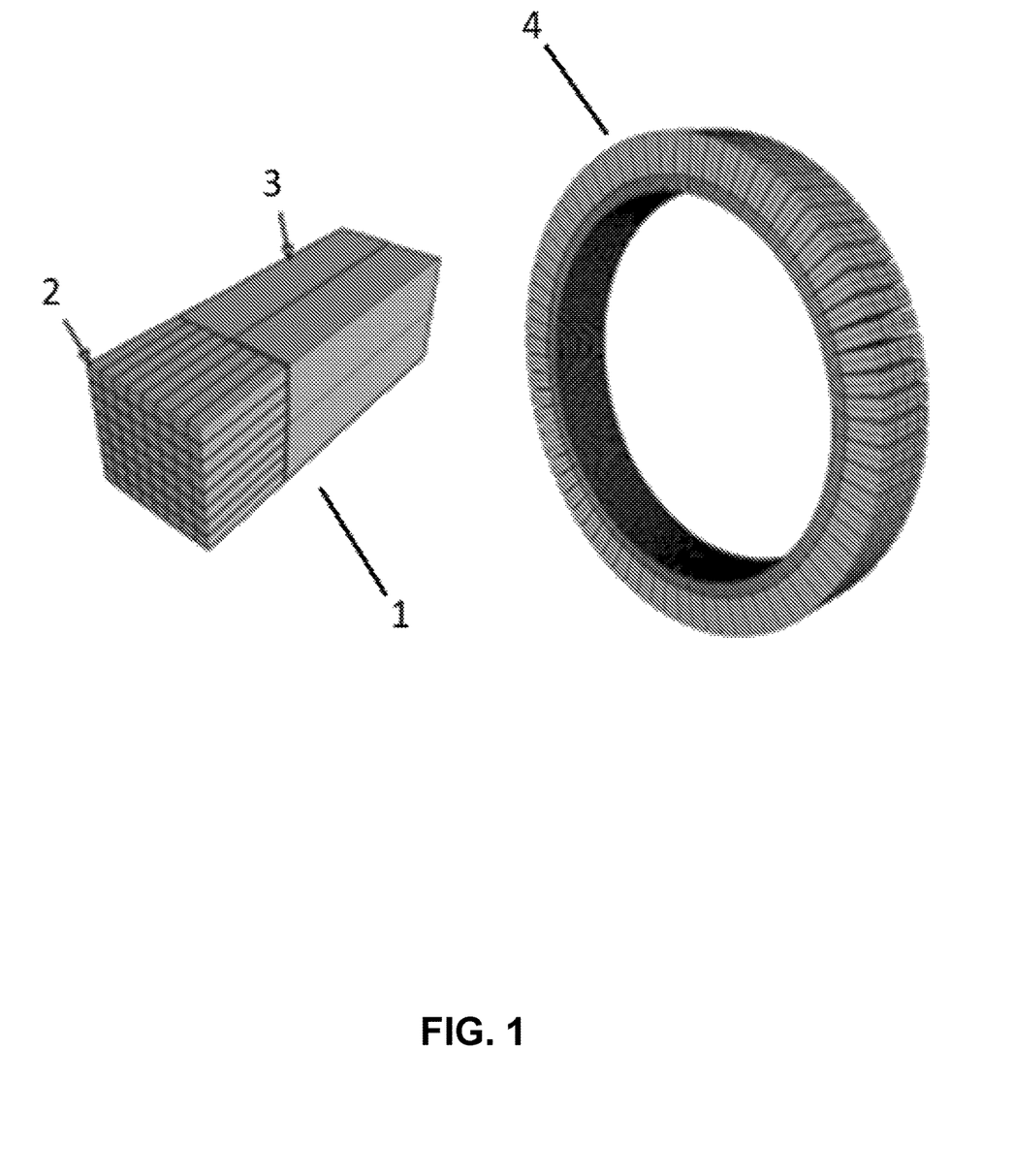

FIG. 1 (left) shows a conventional PET detector block (also referred to herein as a detector module and detector element), which typically comprises a pixelated scintillator crystal element block and associated photon detection sensors, including but not limited to photomultiplier tubes and silicon photomultipliers. If a gamma-ray photon interacts inside one of the crystal elements, detectable scintillation photons are produced and propagate to photon sensors via reflections by crystal surfaces. By the proportion of light detected by the photon sensors, the gamma-ray photon's energy, interaction pixel and interaction time may be estimated. FIG. 1 (right) depicts a detector ring formed from hundreds of detector modules. In medical practice, a detector ring or array is placed around a patient or object to be scanned.

Positioning detectors closer to an object to be scanned, such as a patient, is beneficial in that the solid angle coverage is larger, which can result in higher system sensitivity (i.e., higher percentage of detected gamma-ray photons), shorter scanning times, and/or lower required doses of radioactive tracers. Positioning the detectors closer to the object can also reduce blur caused by non-collinearity (the two gamma rays from annihilation are not perfectly aligned by 180 degree), which leads to better spatial resolution and sharper images.

While positioning detectors closer to objects and patients seems simple, such improved PET systems have not been successfully developed due to several obstacles. For example, placing the detectors closer to an object will result in fewer object samplings (i.e., fewer sample lines connecting different combinations of detector pixels, see FIG. 2), which will result in blurry images and undesirable artifacts.

Figure 3:
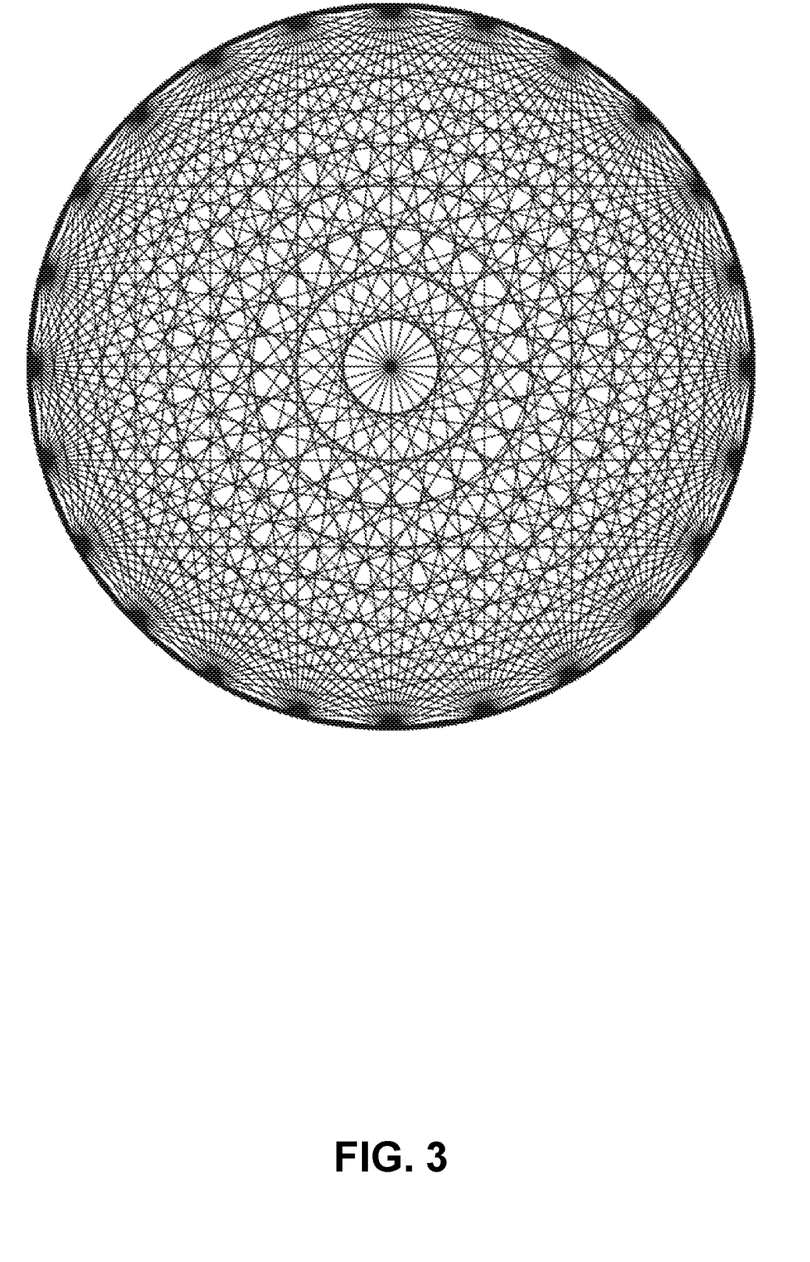
FIG. 3 illustrates the frequency positions within a field of view (FOV) are sampled using an exemplary ring array. As can be seen, certain positions are sampled more frequently that other positions. This disparity is greater at the edge of the FOV.

Additionally, placing the detectors closer to an object or sample (or moving the object or sample closer to the detectors) will also increase non-uniform object sampling leading to non-uniform spatial resolution across the field of view (FOV). More specifically, some positions within the FOV are sampled more frequently than other positions (see FIG. 3 and Moses, William W. "Fundamental limits of spatial resolution in PET." Nuclear Instruments and Methods in Physics Research Section A: Accelerators, Spectrometers, Detectors and Associated Equipment 648 (2011): S236-S240). Placing the detectors closer means that the scanned object, such as the patient's body, will be closer to the edge of the FOV. This will result in more severe blurring caused by unknown depth of interaction (DOI) (see FIG. 4). The blurring is more obvious as the sampling line gets closer to the edge of the FOV.

With specific regard to human and animal patients, how close the detectors can be placed to the patient also depends on the size of the patient or the size of the body part to image. Since different patients will have different sizes, it is challenging to design a system that can accommodate every patient.

Pushed by the need for shorter scan times, accurate diagnostics, and reduced doses of the necessary radioactive tracers, it is highly desirable to improve the sensitivity and spatial resolution of PET systems.

SUMMARY OF THE INVENTION

This invention provides a novel positron emission tomography (PET) system architecture, where the detector modules are placed very close to the patient in order to increase the sensitivity and resolution of the detectors. In an embodiment, the detector modules are adjustable and can be placed closer to the patient according to the patient profile to minimize the distance between the detectors. This technology in combination with high performance PET detectors will make a novel PET scan system with enhanced system sensitivity and spatial resolution.

In an embodiment, the present invention provides a positron emission tomography (PET) system comprising an array of detector modules, wherein at least a portion of the detector modules are positioned on opposing sides of a central space able to accommodate an object to be scanned. Preferably, the front surface of at least a portion of the detector modules are placed within 50 mm of a surface of the object for operation of a PET scan, and the detector modules have a depth of interaction (DOI) capability and a spatial resolution of 4 mm or less. The detector array can be any as generally known in the art, including arrays utilizing scintillation block detectors, flat opposing surfaces, ring arrays, and partial ring arrays.

To overcome the difficulties associated with reduced object samplings, the present invention incorporates detectors having greater spatial resolution (i.e., more and finer crystal elements). As a result, more sampling lines can be formed by different combinations of detector elements since there are more detector elements (see FIG. 2). Furthermore, utilizing detectors having improved spatial resolution and a non-pixel structure will reduce the problems associated with non-uniform sampling since there are a greater number of sampling lines possible by connecting two points on any of two detectors. As a result, the sampling of the FOV will be more uniform. In addition to increasing the spatial resolution, decreasing the crystal element/pixel size can also increase the total samplings of object, which further improves the reconstructed image.

Additionally, the detector modules of the present invention also have depth of interaction (DOI) capability. DOI capability means the detector is able to detect interactions, such as gamma-ray photon interactions, in the depth (Z) direction of the detector in addition to X and Y dimensions (the plane parallel to the impinging plane). The resolution provided by the DOI is preferably similar or close to the in-plane (X-Y) spatial resolution to provide enough information. In an embodiment, the present system has a spatial resolution of 4 mm or less (preferably 3 mm or less, or 2 mm or less). Detectors and detector systems able to provide DOI information and which are suitable for use in the present are described in WO 2018/081404 for "Scintillation detector and associated scintillation detector ring and method".

In an embodiment, the system of the present invention is also designed so that the FOV is adaptable to the shapes and sizes of different patients or different body parts. As a result, the detector modules are able to be placed as close to a patient as possible. In addition, the system is able to be adapted and the detector modules positioned to conform to different body parts. As a result, the system can also serve as an organ-dedicated PET system. For example, in an embodiment, the system is specifically designed to accommodate the chest, abdominal, pelvic, and/or head profile of a human patient.

In an embodiment, the array of detector modules comprises two or more opposing flat panels comprising a plurality of detector modules, where the front surface of the flat panels are placed within 50 mm of a surface of the object for operation of the PET scan. Preferably, at least one of the flat panels is moveable so that the starting operating distance for the PET scan between the opposing flat panels is adjustable.

For conventional clinical PET systems, the distance between the surface of the object to be scanned (i.e., the patient) and the front surface of the detector ranges from 10 cm to 25 cm. The detector crystal element sizes (in the X, Y dimensions) are typically around 2.5 mm×2.5 mm to 4.5 mm×4.5 mm.

In an embodiment of the present invention, the detector modules are able to be positioned so the distance for the PET scan between the surface of the object to be scanned (i.e., the patient) and the front surface of the detector is within 50 mm, preferably within 20 mm, preferably within 10 mm, preferably within 7.5 mm, or preferably within 5 mm. Optionally, the detector modules comprise crystal elements having front surface dimensions (in the X, Y dimensions) less than to 4.0 mm×4.0 mm, preferably less than 2.5×2.5 mm. Preferably, the detectors also have DOI capability in combination with high spatial resolution (i.e., a detector resolution of 4 mm or less, 3 mm or less, 2 mm or less, or preferably 1 mm or less).

In an embodiment, the PET system of the present invention comprises detector modules having direct depth of interaction (DOI) readout capability and high spatial resolution, preferably a spatial resolution less than 4 mm, less than 3 mm, less than 2 mm, or even more preferably less than 1 mm, including in the Z direction. The spatial resolution in the X, Y directions (in-plane resolution) may be the same or different than the resolution in the Z direction (depth resolution). In an embodiment, the spatial resolution in the X and Y directions is less than 3 mm (preferably less than 2 mm or less than 1 mm), while the resolution in the Z direction is less than 4 mm (preferably less than 3 mm or less than 2 mm). There are also no trade-offs between spatial resolution and detector thickness, so better detector spatial resolution can be achieved at no compromise of sensitivity. Optionally, the present invention also has the capability to form an adaptive system able to conform to different patients and patient body parts. In some embodiments, the detector modules of the present invention have a non-pixel structure, such as liquid crystal detectors.

In an embodiment, the present invention also provides a method of performing a positron emission tomography (PET) scan comprising the steps of: a) positioning an object to be scanned within a central space of a PET system, said PET system comprising an array of detector modules, wherein at least a portion of the detector modules are positioned on opposing sides of the central space; b) positioning a front surface of at least a portion of the detector modules within 50 mm of a surface of the object to be scanned, thereby establishing a scanning distance, wherein the detector modules have depth of interaction (DOI) capability and a spatial resolution of 4 mm or less; and c) detecting, with said portion of the detector modules, gamma-rays emitted from a radioactive tracer within the object. Optionally, the method further comprises adjusting the position of the detector modules to be closer to or further away from the object to be scanned, thereby adjusting the scanning distance, where the scanning distance remains within 50 mm of the surface of the object to be scanned.

The methods of the present invention can be utilized with any of the PET systems described herein. For an example, in an embodiment, the method comprises positioning a front surface of at least a portion of the detector modules within 20 mm, within 10 mm, within 7.5 mm, or within 5 mm of a surface of the object to be scanned as in the embodiments described above. In an embodiment, the detector modules comprise crystal elements having front surface dimensions less than to 2.5 mm×2.5 mm.

BRIEF DESCRIPTION OF THE DRAWINGS

The figures referenced throughout the application are specifically incorporated by reference herein.

FIG. 1 (left) shows a conventional PET detector module having a pixelated crystal element block and photomultiplier tubes. FIG. 1 (right) depicts an exemplary detector ring array formed from hundreds of detector modules.

DETAILED DESCRIPTION OF THE INVENTION

In general, the terms and phrases used herein have their art-recognized meaning, which can be found by reference to standard texts, journal references and contexts known to those skilled in the art. Any definitions used herein are provided to clarify their specific use in the context of the invention.

Sensitivity

FIG. 1 (left) shows a conventional PET detector module 1 having crystal elements 2 and photomultiplier tubes 3. Alternative or additional components may be utilized as is known in the art for PET detectors, including but not limited to silicon photomultipliers, collimators, photodiodes, and light guides. If a gamma-ray photon interacts inside one of the crystal elements, detectable scintillation photons are produced and propagate to photon sensors via reflections by crystal surfaces. FIG. 1 (right) depicts a detector array 4 formed in the form of a detector ring comprising a plurality of detector modules 1. In medical practice, a detector array 4 is placed around a patient or object to be scanned.

The sensitivity of current PET system is majorly limited by its small solid angle coverage by the detector ring. If it is possible to push the detector ring closer to the patient, much larger solid angles can be covered and less detector modules are needed.

Figure 2:
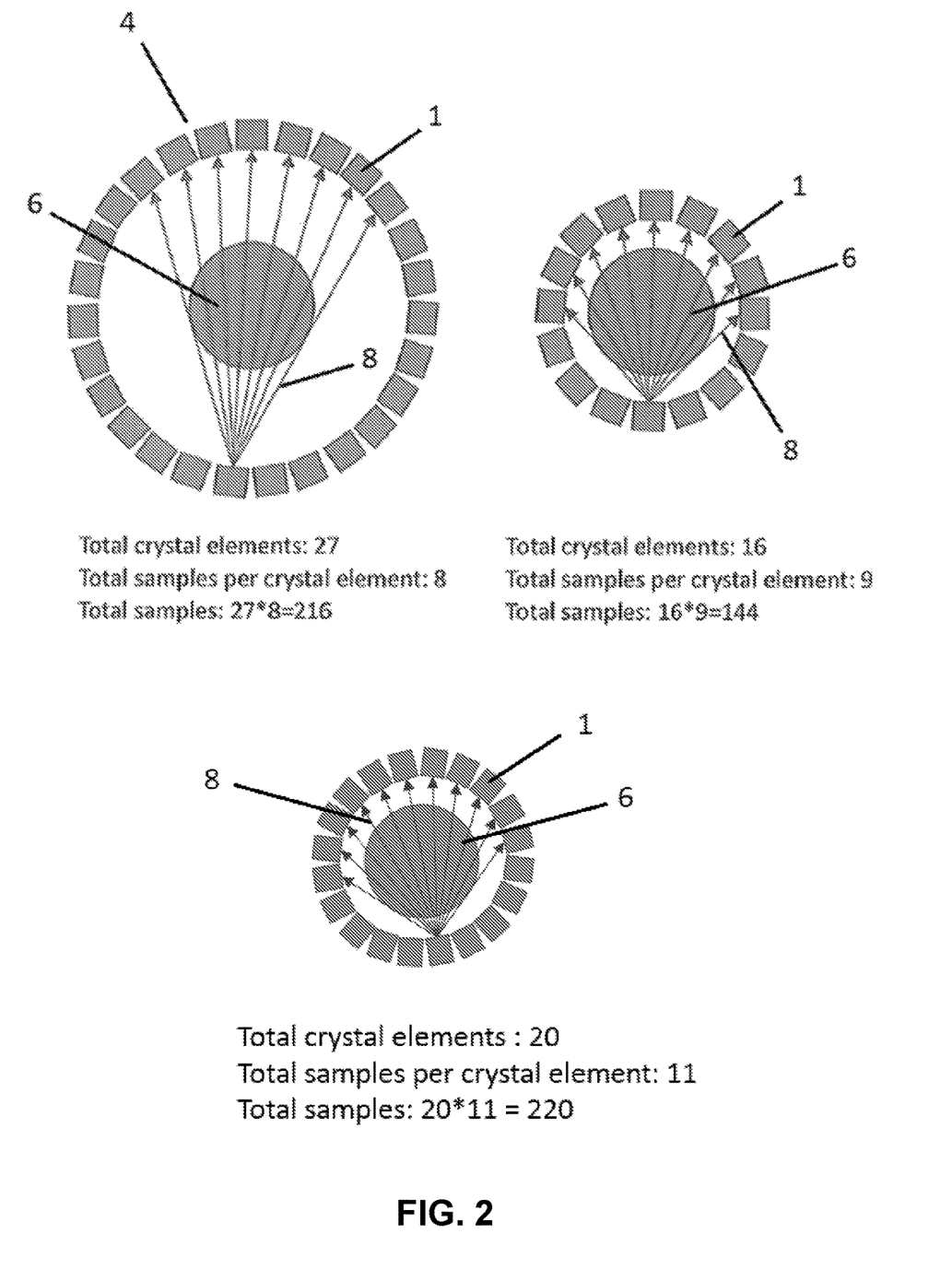
FIG. 2 illustrates exemplary PET systems with detector modules positioned at different distances to an object to be scanned. Each module represents a crystal element in a detector ring. If the crystal elements remain the same size, moving the detector ring closer to the object will result in a decreased total number of samples being available. However, if smaller crystal elements are used, then a greater number of elements can be used which will also increase the total number of samples.

However, to place the detector block closer to the patient, several conditions should be met. Firstly, the PET detector modules should have higher spatial resolution in order to provide enough sampling of the object (i.e., the patient). This is illustrated in FIG. 2, which shows exemplary PET detector arrays 4 with detector modules 1 positioned at different distances to an object or patient 6 to be scanned. Each detector module 1 represents a crystal element in the detector array 4.

If the size of the crystal elements remains the same, shrinking the size of the detector array 4 will reduce the number of sample lines 8 (possible line of responses) of the object. In order to at least maintain the same number of samples of the object, the effective crystal element/pixel size of the detector modules 1 should therefore be smaller, which also means the spatial resolution of the detector module 1 would need to be improved (see FIG. 2).

Figure 4:
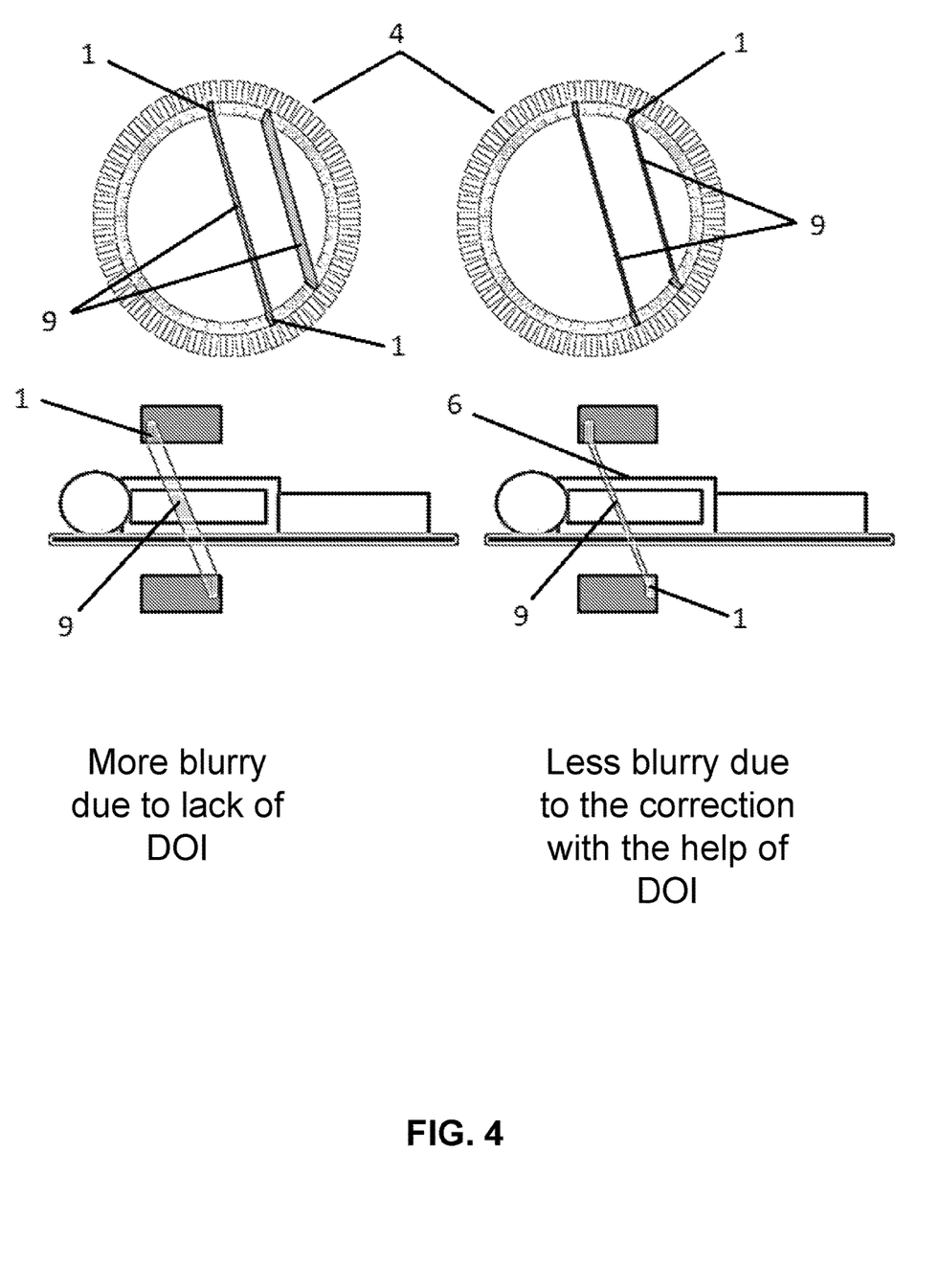
FIG. 4 illustrates two exemplary PET systems in an embodiment of the present invention. One PET system (left) contains more blur and a greater sample volume due to the absence of DOI capability, while the other PET system (right) contains DOI correction and contains less blur.

Secondly, to place the detector module closer to the patient, the PET detector module should preferably also have depth of interaction (DOI) capability. Additional means for providing DOI capability to a PET system are generally known in the art (see, for example, Ito et al., Biomed Eng Lett (2011) 1:70-81; and Morrocchi et al. EJNMMI Physics (2017) 4:11). FIG. 4 shows two exemplary PET detector arrays 4, where blur is due to the greater sampling volume 9 between the two detector modules 1. If these two detector modules 1 have coincidence signals, a line of response should connect these two crystal elements, which indicates the possible locations for the annihilation to happen. Without DOI, this line of response could be any line connecting any pair of positions in these two crystal elements (see FIG. 4, left). However, if with DOI the depth in the crystal elements of these two coincident interaction positions is known, then the crystal region can be narrowed down and the ambiguity is reduced. As a result, the sampling volume 9 indicating the possible line of responses is reduced (FIG. 4, right).

Figure 5:
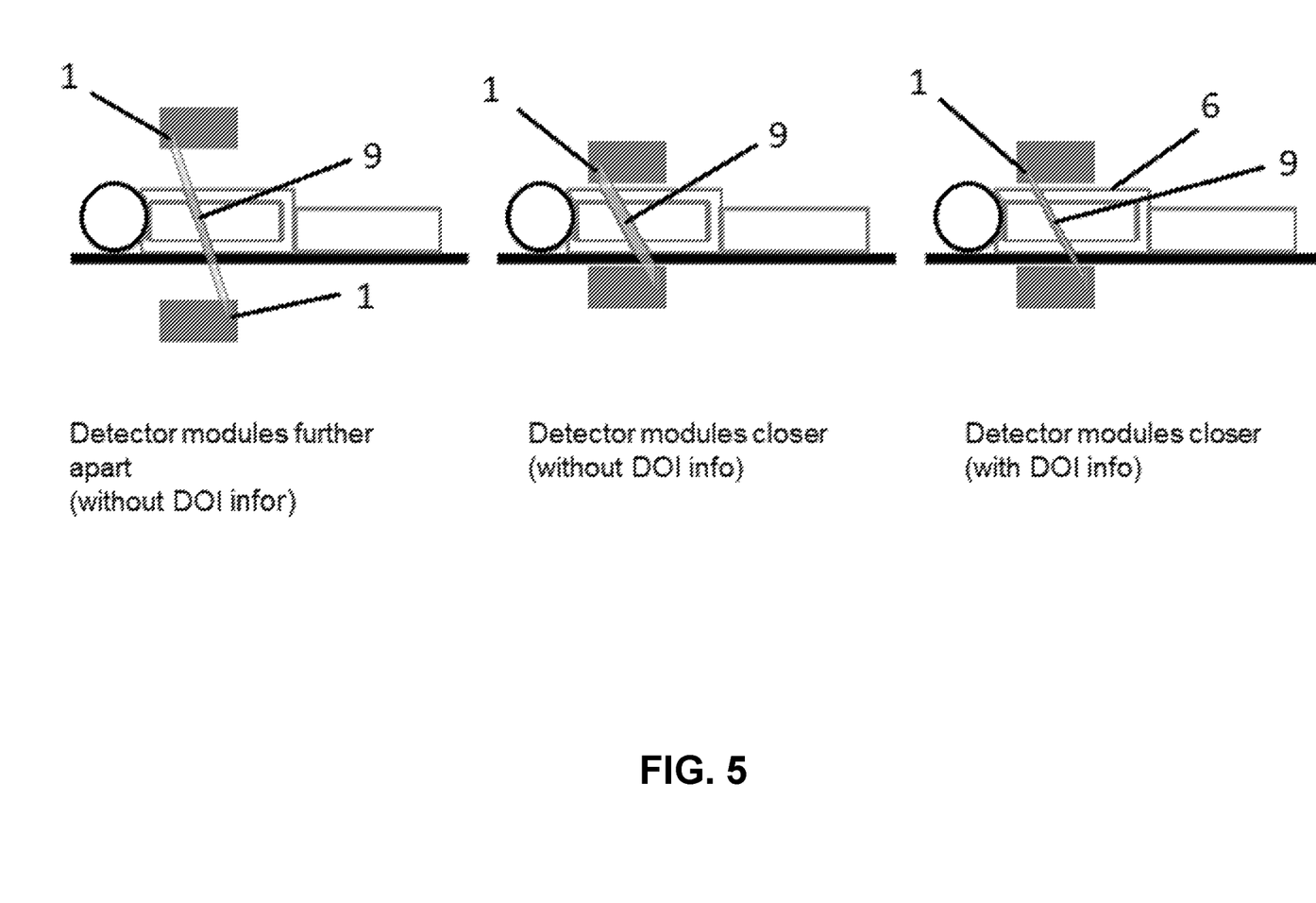
FIG. 5 illustrates exemplary PET systems in an embodiment of the present invention positioned in relation to a patient. In the system illustrated on the left, the detector modules are positioned further apart and do not contain any DOI information. In the system illustrated in the middle, which also does not contain any DOI information, the detector modules are positioned closer to the patient resulting in an increase in blur, which is seen in the wider sampling volume. In the system illustrated on the right, the detector modules are positioned at the same close distance as the middle system; however, because this system incorporates DOI information, the blur is reduced.

Additionally, more blur can be present between two crystal pixels at different axial locations. For example, the sample volume 9 will increase and blur will typically become more significant as the detector modules 1 are positioned closer towards the patient 6 (see FIG. 5, left and middle figures). However, if the detectors have DOI capability, this effect will be greatly mitigated, so that detector modules 1 can be positioned closer to patient 6 while limiting the amount of blur.

Spatial Resolution

Figure 6:
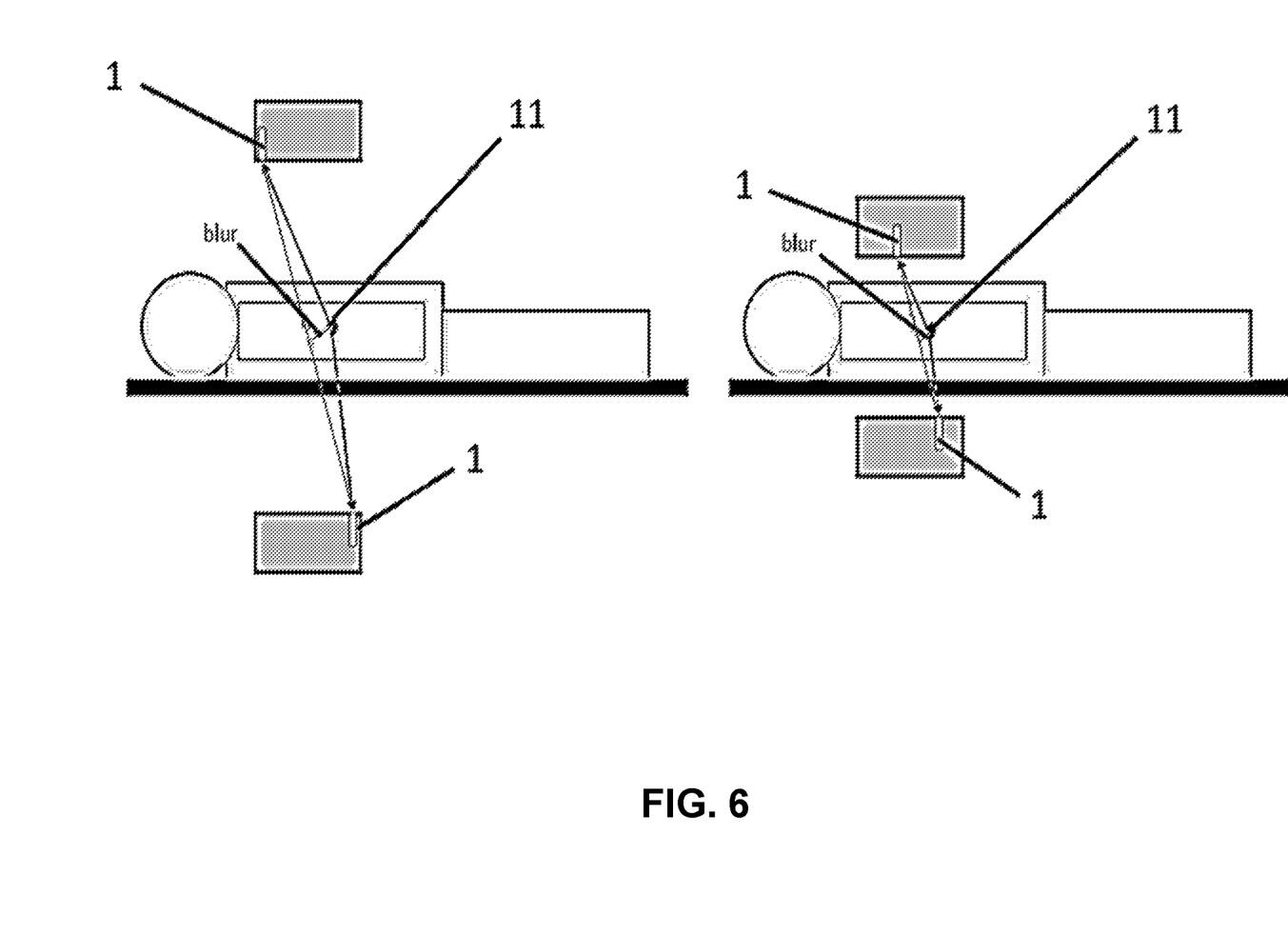
FIG. 6 illustrates two exemplary PET systems in an embodiment of the present invention positioned at different distances to a patient, each PET system having detector modules located on opposite sides of the patient. The position of a detected particle within the patient is approximated according to a line between two opposing detector modules. However, the top detector module, the particle detected within the patient, and the bottom detector module may not be located in a perfect line (i.e., they are not collinear). As a result of the potential difference between the approximate particle position and the actual particle position, blur will occur.

The spatial resolution of PET system is partially limited by the non-collinearity effect. Since this effect is proportional to the distance between the two detector modules detecting the two coincidence photons (blur~$0.0022D$), if the detector modules can be pushed closer to the patient, the non-collinearity effect will also be mitigated, which reduces this hard physical limitation. FIG. 6 shows two exemplary PET systems where the detector modules 1 are positioned at different distances to a patient. The position of a detected particle 11 within the patient is approximated according to a line between two opposing detector modules 1. However, the top detector module, the particle 11 detected within the patient, and the bottom detector module may not be located in a perfect line (i.e., they are not collinear). As a result of the potential difference between the approximate particle position and the actual particle position, blur will occur.

Accordingly, the benefits of close-range PET system will only emerge if the detector module has simultaneously both improved spatial resolution and DOI capability.

Exemplary Designs of a Close-Range PET System

In an embodiment, the present invention provides close-range PET systems where, as compared with conventional PET systems, the detector modules are placed much closer to the object to be scanned in order to minimize the distance between the surface of the object to the detector module surface. The detector modules are designed to have both improved in-plane spatial resolution, as well as DOI resolution at the same time, which allows the detector modules to be moved closer to the object in order to boost sensitivity and resolution.

Figure 7:
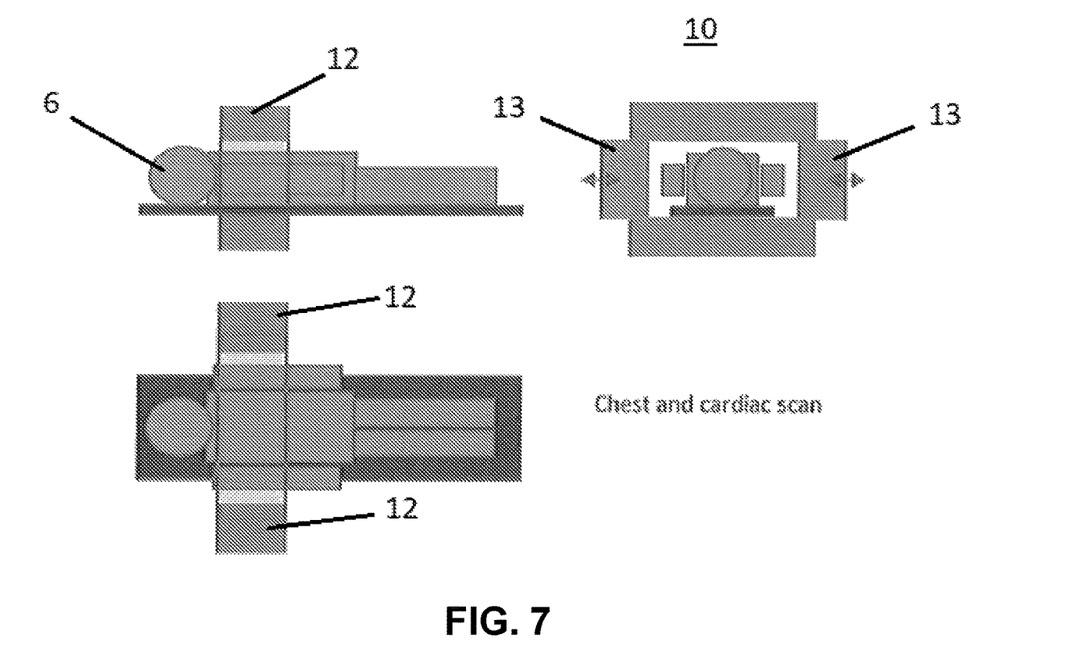
FIGS. 7-10 illustrate close-range PET systems in certain embodiments of the present invention. Close-range PET systems are illustrated for chest and cardiac scans (FIG. 7), abdominal scans (FIG. 8), prostate and pelvic scans (FIG. 9), and head scans (FIG. 10). The close-range PET systems position the detector panels closer to the patient than conventional PET systems, or comprise two or more moveable detector panels placed on opposing sides of the patient that are able to be moved closer to the patient.
Figure 8:
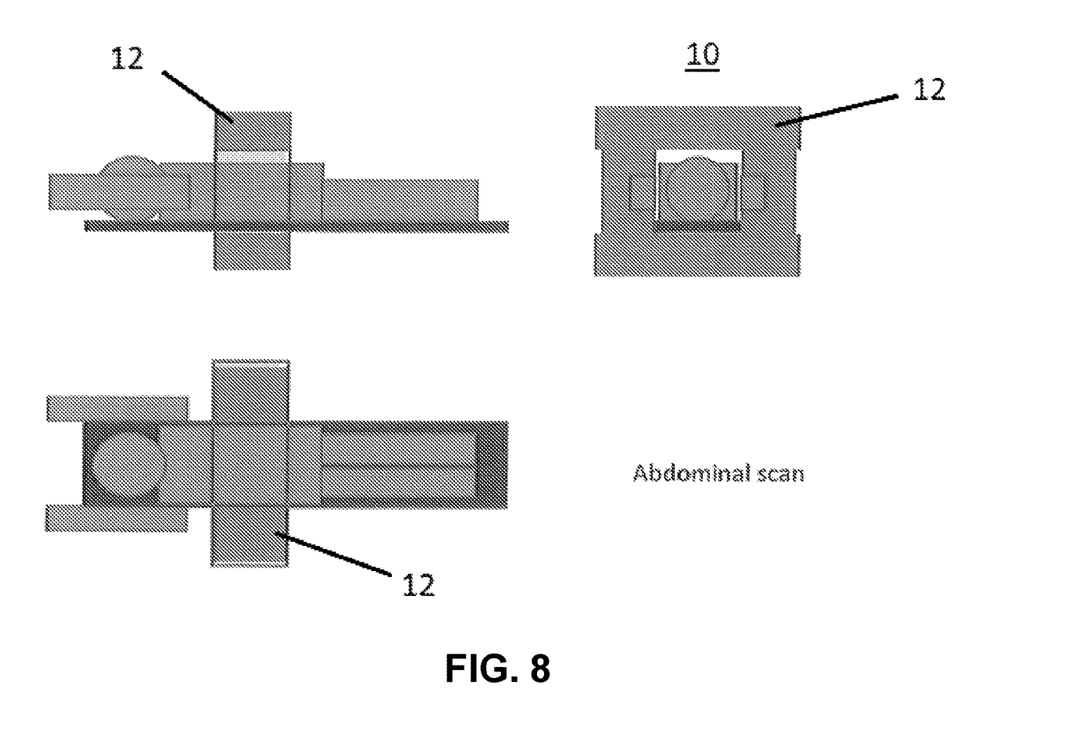
Figure 9:
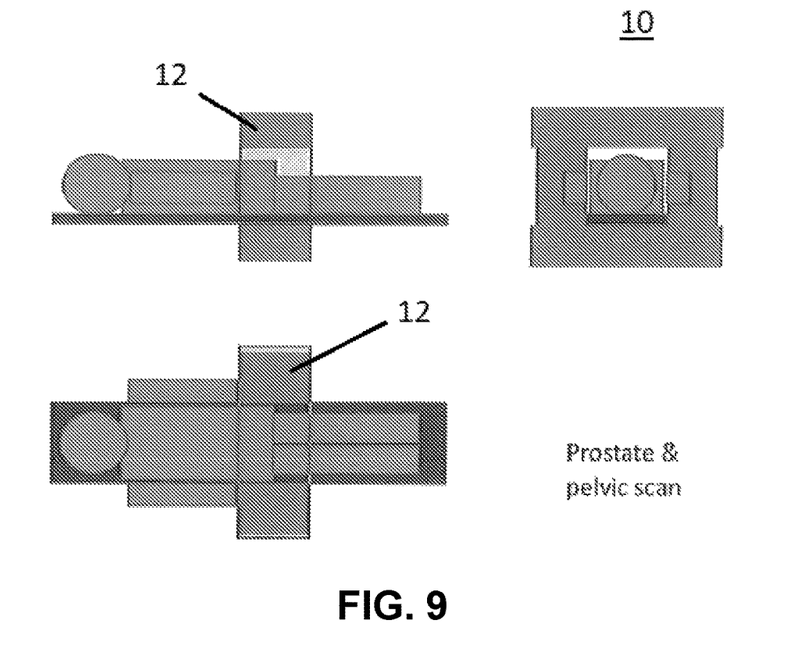
Figure 10:
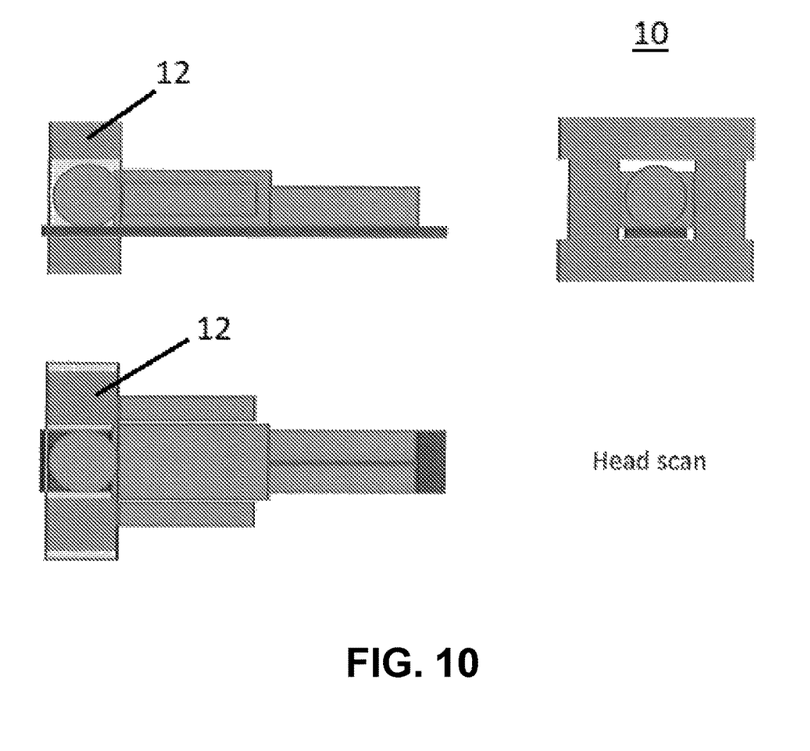

Exemplary PET systems 10 are shown in FIG. 7 (for chest and cardiac scans), FIG. 8 (for abdominal scans), FIG. 9 (for prostate and pelvic scans), and FIG. 10 (for head scans). Preferably, the object 6 to be scanned is a patient or body part. The PET system 10 comprises two or more detector panels 12 placed on at least two sides of the object 6 to be scanned. Preferably, the detector panels are moveable detector panels 13, wherein the moveable detector panels 13 are able to be moved closer to or further away from the object to be scanned. As a result, the PET system is able to adapt to objects, patients, or body parts having different widths.

Figure 11:
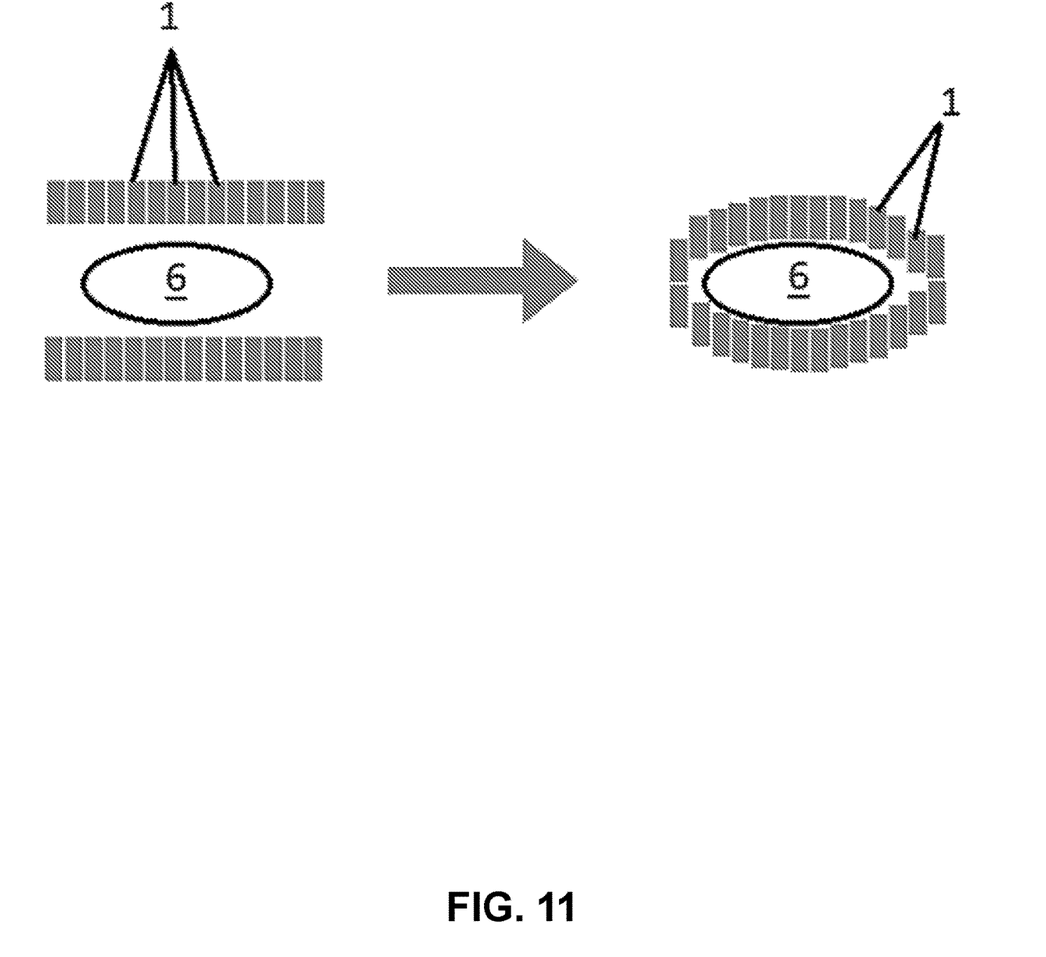
FIG. 11 illustrates a detector array in an embodiment of the present invention where individual detector modules are adjustable and can be positioned to conform to the shape and size of the object to be imaged.

Although moveable detector panels are only illustrated in FIG. 7, moveable detector panels can be used for any of the detector panels described in FIGS. 7-10. The detector panels 12 and 13 depicted in FIGS. 7-10 are generally flat panels formed by the detector blocks, with distance between the detector panels 12 and 13 being designed or adjustable to be suitable for a specific use (e.g., chest scans and head scans). Alternatively, as shown in FIG. 11, the detector array may have a plurality of detector modules 1 that are individually adjustable and are able to be positioned to conform to the shape and size of the object 6 to be imaged.

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents or components is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a size range, a number range, a thickness range, or a composition range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when devices are claimed, it should be understood that devices known and available in the art prior to Applicant's invention, including devices for which an enabling disclosure is provided in the references cited herein, are not intended to be included in the device claims herein.

As used herein, "comprising" is synonymous with "including," "containing," or "characterized by," and is inclusive or open-ended and does not exclude additional, unrecited elements or method steps. As used herein, "consisting of" excludes any element, step, or component not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, components, configurations, detectors, and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

I claim:

1. A positron emission tomography (PET) system comprising an array of detector modules, wherein at least a portion of the detector modules are positioned on opposing sides of a central space able to accommodate an object to be scanned,
    wherein a front surface of at least a portion of the detector modules are placed within 20 mm of a surface of the object for operation of a PET scan, and
    wherein the detector modules are scintillation block detectors comprising crystal elements having front surface dimensions less than 2.5 mm×2.5 mm, and have depth of interaction (DOI) capability, an in-plane spatial resolution of 3 mm or less, and a depth resolution of 4 mm or less.

2. The system of claim 1 wherein a front surface of the detector modules are placed within 10 mm of a surface of the object for operation of the PET scan.

3. The system of claim 1 wherein a front surface of the detector modules are placed within 5 mm of a surface of the object for operation of the PET scan.

4. The system of claim 1 wherein the detector modules have a spatial resolution of 2 mm or less.

5. The system of claim 1 wherein the detector modules have an in-plane spatial resolution of 2 mm or less, and a depth resolution of 3 mm or less.

6. The system of claim 1 wherein the array of detector modules is arranged in a ring or partial ring around the central space.

7. The system of claim 1 wherein the array of detector modules comprises two or more opposing flat panels comprising a plurality of detector modules, wherein a front surface of at least a portion of the detector modules of the flat panels are placed within 20 mm of a surface of the object for operation of the PET scan.

8. The system of claim 7 wherein at least one of the flat panels is moveable so that the starting operating distance for the PET scan between the opposing flat panels is adjustable.

9. The system of claim 1 wherein at least a portion of the detector modules are adjustable and are able to move closer to or further away from the object for operation of the PET scan.

10. The system of claim 1 wherein the object to be scanned is a human patient.

11. The system of claim 1 wherein the system is designed to accommodate a chest, abdominal, pelvic, and/or head profile of a human patient.

12. The system of claim 1 wherein the detector modules have an in-plane spatial resolution of 1 mm or less, and a depth resolution of 1 mm or less.

13. A method of performing a positron emission tomography (PET) scan comprising the steps of:
 a) positioning an object to be scanned within a central space of a PET system, said PET system comprising an array of detector modules, wherein at least a portion of the detector modules are positioned on opposing sides of the central space;
 b) positioning a front surface of at least a portion of the detector modules within 20 mm of a surface of the object to be scanned, thereby establishing a scanning distance, wherein the detector modules are scintillation block detectors comprising crystal elements having front surface dimensions less than 2.5 mm×2.5 mm, and have depth of interaction (DOI) capability, an in-plane spatial resolution of 3 mm or less, and a depth resolution of 4 mm or less; and
 c) detecting, with said portion of the detector modules, gamma-rays emitted from a radioactive tracer within the object.

14. The method of claim 13 further comprising adjusting the position of said portion of the detector modules to be closer to or further away from the object to be scanned, thereby adjusting the scanning distance, wherein the scanning distance remains within 20 mm of the surface of the object to be scanned.

15. The method of claim 13 wherein the scanning distance is within 5 mm of the surface of the object to be scanned.

16. The method of claim 13 wherein the object to be scanned is a human patient, and wherein the array of detector modules are able to accommodate a body part of a human patient so that the scanning distance remains within 20 mm of a surface of the body part to be scanned.

17. A positron emission tomography (PET) system comprising an array of detector modules, wherein at least a portion of the detector modules are positioned on opposing sides of a central space able to accommodate an object to be scanned,
 wherein a front surface of at least a portion of the detector modules are placed within 20 mm of a surface of the object for operation of a PET scan, and
 wherein the detector modules are liquid crystal detectors having a non-pixel structure, wherein the detector modules have depth of interaction (DOI) capability, an in-plane spatial resolution of 3 mm or less, and a depth resolution of 4 mm or less.

18. The system of claim 17 wherein the detector modules have an in-plane spatial resolution of 1 mm or less, and a depth resolution of 1 mm or less.

19. The system of claim 17 wherein the array of detector modules is arranged in a ring or partial ring around the central space.

20. The system of claim 17 wherein the array of detector modules comprises two or more opposing flat panels comprising a plurality of detector modules, wherein at least one of the flat panels is moveable so that the starting operating distance for the PET scan between the opposing flat panels is adjustable.

\* \* \* \* \*